(12) United States Patent
Henson et al.

(10) Patent No.: US 6,509,050 B1
(45) Date of Patent: Jan. 21, 2003

(54) USE OF ANTIMICROBIAL POLYPHOSPHATES IN FOOD PROCESSING

(75) Inventors: Lulu S. Henson, Plainsboro, NJ (US); Robert V. Manley, Yardley, PA (US); Kevin J. Fennewald, Ballwin, MO (US)

(73) Assignee: Astaris LLC, St. Louis, MO (US)

( * ) Notice: Subject to any disclaimer, the term of this patent is extended or adjusted under 35 U.S.C. 154(b) by 0 days.

(21) Appl. No.: 09/621,776

(22) Filed: Jul. 21, 2000

Related U.S. Application Data (60) Provisional application No. 60/145,151, filed on Jul. 22, 1999.

(51) Int. Cl.$^7$ .......................... A23B 4/027; A23L 1/314
(52) U.S. Cl. ....................... 426/332; 426/335; 426/641; 426/652
(58) Field of Search ................................. 426/332, 335, 426/641, 652

(56) References Cited

U.S. PATENT DOCUMENTS

| | | | |
|---|---|---|---|
| 3,029,150 A | 4/1962 | Bickel et al. | |
| 3,681,091 A | 8/1972 | Kohl et al. | |
| 3,958,026 A | 5/1976 | Leone et al. | 426/332 |
| 4,356,203 A | 10/1982 | Ueno et al. | 426/266 |
| 4,431,679 A | 2/1984 | Crawford | 426/332 |
| 4,781,934 A | 11/1988 | Shimp et al. | 426/264 |
| 4,937,092 A | 6/1990 | Brotsky et al. | 426/643 |
| 4,948,621 A | 8/1990 | Schwartz | 426/652 |
| 4,971,822 A | 11/1990 | Michel et al. | 426/332 |
| 5,069,922 A | 12/1991 | Brotsky et al. | 426/332 |
| 5,364,650 A | 11/1994 | Guthery | 426/331 |
| 5,490,992 A | 2/1996 | Andrews et al. | 424/606 |
| 5,635,231 A | 6/1997 | Bender et al. | 426/332 |
| 5,641,530 A | 6/1997 | Chen | 426/532 |

FOREIGN PATENT DOCUMENTS

| | | |
|---|---|---|
| CN | 1097576 | 1/1995 |
| DE | 43 05 105 C1 | 8/1994 |
| EP | 0 397 590 | 11/1990 |
| EP | 0 985 349 A2 | 8/1999 |
| EP | 0 985 349 A3 | 3/2000 |
| GB | 2 187 081 | 1/1987 |
| JP | 55-15728 | 2/1980 |
| JP | 09028361 | 4/1997 |

OTHER PUBLICATIONS

Elliott, Paul R.; Straka, Robert P.; Garibladi, John A. "Polyphosphate Inhibition of Growth of Pseudomonads From Poultry Meat" *Applied Microbiology*. 1964, vol. 12, pp. 517–522.

Knabel, S.J.; Walker, H.W. and Hartman, P.A., "Inhibition of *Aspergillus flavus* and Selected Gram–positive Bacteria by Chealiton of Essential Metal Cations by Polyphosphates", *Journal of Food Production*. May 1991, vol. 54, No. 5, pp. 360–365.

Obafemi, A.; Davies, R. "Effect of Polyphosphates on the Survival of Pre–stressed *Salmonella typhimurium* Cells in Frozen Chicken Meat" *Food Chemistry*. 1985, vol. 18, pp. 179–191.

Lee, Ruby M.; Hartman, Paul A.; Olson, Dennis G.; Williams, Fred D., "Bactericidal and Bacteriolytic Effects of Selected Food–Grade Phosphates, Using *Staphylococcus aureus* as a Model System", *Journal of Food Production*. Apr. 1994, vol. 57, No. 4, pp. 276–283.

Molins, R.A.; Kraft, A.A.; Olson, D.G. and Hotchkiss, D.K., "Recovery of Selected Bacteria in Media Containing 0.5% Food Grade Poly– and Pyrophosphates" *Journal of Food Science*, Apr. 1994, vol. 49, p. 984.

Shelef, L.A., "The Shelf Life of Food and Beverages" *Proceedings of the Fourth International Flavor Conference*, Jul. 1985, pp. 691–703.

Zaika, Laura L. and Kim, Anna H. "Effect of Sodium Polyphosphates on Growth of *Listeria monocytogenes*" *Journal of Food Protection*, Jul. 1993, pp. 577–580.

Abstract—Marcy, J.A.; Kraft, A.A.; Hotchkiss, D.K.; Molins, R.A.; Olson, D.G.; Walker, H.W.; Merkenich, K. "Effects of Selected Commercial Phosphate Products on the Natural Bacterial Flora of a Cooked Meat System", *Journal of Food Science*, 1988, vol. 53, pp. 391–393.

Madril, M.T.; Sofos, J.N. "Interaction of Reduced NaC, Sodium Acid Pyrophosphate and pH on the Antimicrobial Activity of Comminuted Meat Products" *Journal of Food Science*. 1986, vol. 51, pp. 1147–1151.

Abstract—Madril, M.T.; Sofos, J.N. "Interaction of Reduced NaC, Sodium Acid Pyrophosphate and pH on the Antimicrobial Acitvity of Comminuted Meat Products" *Journal of Food Science* 1986, vol. 51, pp. 1147–1151.

Madril, M.T. and Sofos, J.N. "Antimicrobial and Functional Effects of Six Polyphosphates in Reduced NaC Comminuted Meat Products" *Lebensm Wiss. U. Technol.* 1985, vol. 18, pp. 326–322.

Abstract—Molins, R.A.; Kraft, A.A.; Walker, H.W.; Rust, R.E.; Olson, D.G.; Merkenich, K.; "Effect of Inorganic Polyphosphates on Ground Beef Characteristics: Microbiological Effects on Frozen Beef Patties" *Journal of Food Science* 1987, vol. 52, pp. 46–49.

(List continued on next page.)

Primary Examiner—Arthur L. Corbin
(74) Attorney, Agent, or Firm—Thompson Coburn LLP (57) ABSTRACT

Polyphosphates control the growth of bacteria during food processing. These compositions comprise antimicrobial polyphosphates alone or in combination with organic acids and/or their salts and are effective in food-related applications, including: cleaning compositions to disinfect the surface of food and to clean and disinfect equipment used in food processing, and compositions to be added to food to inhibit the growth of microorganisms responsible for foodborne diseases and spoilage during distribution and storage.

16 Claims, 5 Drawing Sheets

OTHER PUBLICATIONS

Abstract—Marcy, J.A.; Kraft, A.A.; Hotchkiss, D.K.; Molins, R.A.; Olson, D.G.; Walker, H.W.; White, P.J.; "Effect of Acid and Alkaline Pyrophosphate Blends on the Natural Flora of a Cooked Meat System" *Journal of Food Science* 1988, vol. 53, pp. 25–27.

Marcy, J.A.; Kraft, A.A.; Hotchkiss, D.K.; Molins, R.A.; Olson, D.G.; Walker, H.W.; White, P.J.; "Effect of Acid and Alkaline Pyrophosphate Blends on the Natural Flora of a Cooked Meat System" *Journal of Food Science* 1988, vol. 53, pp. 25–27.

Abstract—Marcy, J.A.; Kraft, A.A.; Hotchkiss, D.K.; Molins, R.A.; Olson, D.G.; Walker, H.W.; White, P.J.; "Effect of Acid and Neutral Pyrophosphates on the Natural Bacterial Flora of a Cooked Meat System" *Journal of Food Science* 1988, vol. 53, pp. 28–30.

Abstract—Molins, R.A.; Kraft, A.A.; Marcy, J.A. "Extension of Shelf–life of Fresh Ground Pork with Pyrophosphates" *Journal of Food Science* 1987, vol. 52, pp. 513–514.

Abstract—Choi, Y.I.; Kastner, C.L.; Kropf, D.H. "Effects of Hot Boning and Various Levels of Salt and Phosphate on Microbial, TBA, and pH Values of Preblended Pork During Cooler Storage" *Journal of Food Protection,* 1987, vol. 50, pp. 1037–1043.

Abstract—Flores, L.M.; Summer, S.S.; Peters, D.L.; Mandigo, R. "Evaluation of a Phosphate to Control Pathogen Growth in Fresh and Processed Meat Products" *Journal of Food Protection ,* 1996, vol. 59, pp. 356–359.

Abstract—Molins, R.A.; Kraft, A.A.; Walker, H.W.; Olson, D.G.; "Effect of Poly– and Pyrophosphates on the Natural Bacterial Flora and Inoculated *Clostirium sporogenes* PA 3679 in cooked vacuum packaged Bratwurst" *Journal of Food Science.* 1985, vol. 50, pp. 876–800.

Lee, Ruby M.; Hartman, Paul A.; Olson, Dennis G.; Williams, Fred D. "Bacterial and Bacteriolytic Effects of Selected Food–Grade Phosphates, Using *Staphylococcus aureus* as a Model system" *Journal of Food Protection.* Apr. 1994, vol. 57, pp. 276–283.

Vareltzis K., "Antimicrobial effects of sodium tripolyphosphate against bacteria attached to the surface of chicken carcasses", Lebensmittel–Wissenschaft und–technologie, vol. 30, No. 7, 1997, pp. 665–669.

Handbook of Food Additives, $2^{nd}$ edition, CRC Press, Cleveland, Ohio, 1972 (p. 621, 626, 628–631, 647 and 738–742).

USE OF ANTIMICROBIAL POLYPHOSPHATES IN FOOD PROCESSING

This appplication claims the benefit of Ser. No. 60/145,151, filed Jul. 22, 1999.

FIELD OF THE INVENTION

This invention relates to polyphosphates and their use in controlling the growth of bacteria. In particular, this invention relates to the use of antimicrobial polyphosphates to control the growth of bacteria in foods or during food processing.

BACKGROUND OF THE INVENTION

In this specification and claims, unless the context indicates otherwise, "food" means any liquid, solid, semi-solid, dispersion, suspension or emulsion, including those controlled by the Federal Food, Drug and Cosmetic Act, which are consumable by mammals (including animals and humans), fish and other marine life, and fowl, whether or not having nutritive value, and which are susceptible to microbial growth. "Foods" therefore include proteinaceous substances and/or carbohydrates, beverages, edible oils and water, including directly consumable water, e.g., bottled water, and water used to prepare, process or transport other food forms.

Bacterial contamination of food is a major problem in the food processing industry. Bacteria must be controlled throughout the food processing process, for example: (1) surface treatment of foods to disinfect the surface and kill spoilage organisms and pathogens located on the surface of the food; (2) in food processing plants, such as dairy, meat, and poultry processing facilities, to kill spoilage organisms and pathogens in the food processing equipment; and (3) in the processed food to prevent the growth of spoilage organisms and pathogens during distribution and storage.

Strong oxidants, such as peracetic acid and hydrogen peroxide are used to control bacteria in food processing plants. See, for example, Chen, U.S. Pat. No. 5,641,530, which discloses the use of mixtures comprising hydrogen peroxide as disinfectants in food-related applications. However, strong oxidants pose a hazard to the user because they can attack the skin. Hydrogen peroxide cannot be incorporated into processed food to protect it from bacterial contamination and growth during storage and distribution. Peracetic acid solutions are acidic and can corrode equipment. Peracetic acid decomposes to acetic acid, which can adversely affect the taste and odor of the food. Other cleaning products typically have a pH of 10.5 to 12 and are likely to damage the skin, eyes, and respiratory passages upon contact or inhalation.

Guthery, U.S. Pat. No. 5,364,650, discloses a method for disinfecting animal carcasses by dipping them in a solution comprising aliphatic medium chain fatty acids, a chelating agent, and hydrochloric acid. This solution is acidic and potentially harmful to the skin, eyes, and respiratory passages. Bender, U.S. Pat. No. 5,635,231, discloses a method for disinfecting animal carcasses by treating them with an alkali metal orthophosphate and steam. This method is difficult to use because of the need to generate steam and the high concentration of alkali metal phosphate required for efficacy.

Lactic acid and its sodium and potassium salts are incorporated into food as antimicrobials. However, at least 2% by weight, and typically 3% by weight, of lactic acid is required, which can adversely affect taste. If lactic acid is added, the lowered pH produced by the added lactic acid can also reduce the water holding capacity of meat.

Thus, a need exists for non-corrosive materials that can be used to control bacteria on the surface of food, in food processing plants, and that can be incorporated into food to protect it from bacterial contamination and growth during storage and distribution.

SUMMARY OF THE INVENTION

It has been discovered that treatments of alkali metal orthophosphate, tripolyphosphate, acid pyrophosphates, polyphosphate, and pyrophosphate, either singly or as mixtures thereof, can be used to reduce and control various classes of microorganisms, specifically those important to the safety and spoilage of food during processing, storage, and distribution. Gram-negative organisms belonging to, but not restricted to, the genera Escherichia, Salmonella, and Pseudomonas, are generally adversely affected by compositions that are alkaline and contain polyphosphates. Gram-positive organisms belonging to, but not restricted to, the genera Staphylococcus and Listeria are generally adversely affected by compositions that contain polyphosphates and are alkaline or neutral. Because these compositions control pathogens at near neutral pH conditions using very dilute preparations, the physicochemical changes (color, texture, flavor, nutrient retention) that may occur at highly alkaline or highly acidic conditions are reduced. These compositions are safer to handle and have fewer disposal problems than highly alkaline or highly acidic compositions.

These compositions can be used in food-related applications, including: cleaning compositions to disinfect the surface of food and to clean and disinfect equipment used in food processing and solutions to be added to food to inhibit the growth of microorganisms responsible for food-borne diseases and spoilage during distribution and storage.

Optionally, the compositions may contain at least one organic acid and/or at least one salt of an organic acid, for synergistic antimicrobial action in foods.

DETAILED DESCRIPTION OF THE INVENTION

Specific glassy polyphosphates are more effective against certain microorganisms especially those that are important to food safety. While not being bound by any theory or explanation, it is postulated that these polyphosphates induce changes in the transport and availability of vital nutrients to the cell, thereby preventing normal metabolic processes from occurring. This leads eventually to cell death or injury.

Compositions that are inhibitory to microorganisms may range from 0.05% to 3%, preferably from 0.1% to 1%. The treatment of the food may involve addition of the composition to the food such that the composition becomes distributed inside the food. Alternatively, the composition may be added only to the surface of the food or a combination of both treatments may be employed. Synergies may be expected to occur in raw muscle foods or in any fresh foodstuff that contain phosphatases with certain spices and their extracts such as garlic and onions by minimizing the hydrolysis of the glassy polyphosphate. Polyphosphates preserve the color and vitamin content of fruits and vegetables, raw and precooked meat, poultry, and seafood products. Polyphosphates also provide moisture retention, flavor protection, and emulsion stability to meat and poultry products.

Phosphate-Organic Acid and/or Salt Combinations

There is an antimicrobial synergy between phosphates and organic acids and/or salts of organic acids, especially lactic acid and/or its salts, such that the effective total concentrations required to obtain microbial efficacy in meat, poultry, and seafood products will be reduced. The polyphosphate has a chain length of at least 2, preferably 3 to 100, is water soluble, and is a sodium salt, a potassium salt, a mixed sodium/potassium salt, a mixture of sodium and potassium salts, or a mixture of sodium, potassium, and mixed sodium/potassium salts. Suitable organic acids are edible organic acids, such as lactic acid, citric acid, acetic acid, malic acid, fumaric acid, etc., and the salts thereof likewise are edible salts. Sodium and potassium salts of edible organic acids are preferred. Salts of lactic acid are more preferred. These acids and/or salts are generally added so that the resulting meat, poultry, or seafood product comprises 0.3% to 7% by weight thereof, preferably 1% to 3%, more preferably 0.3% to 2.0%, by weight thereof. Phosphates will be effective at concentrations of 0.1% to 2% by weight, preferably 0.5% to 1.0% by weight in the final meat, poultry, or seafood product. Because the total amount of phosphate and acid and/or salt added is reduced, it is less likely that these materials will cause changes in the aesthetic properties of the meat, poultry, and seafood products.

The solution may be added to either cured or uncured, cooked or uncooked, fresh, or raw meat, poultry, or seafood. Cured products contain added nitrites or nitrates, compounds that are known to be inhibitory to *Clostridium botulinum*. Hence, for cured products, it may be expected that lower levels of acid salt and phosphate will be required to obtain antimicrobial efficacy. For both fresh and cooked products, the combination of acid and/or acid salts and phosphate may be incorporated to the product either through injection, vacuum tumbling, surface treatment or by any combination of these methods. If incorporated by injection and/or vacuum tumbling, it is common practice to add the solution containing the phosphate and acid salt to the raw or fresh product before cooking. Products intended to be sold raw, either fresh or previously frozen, may likewise be injected or vacuum tumbled with phosphate only or the combination of acid and/or salt thereof and phosphate.

The solution is typically prepared by first dissolving the phosphate in water followed by salt (NaCl), nitrites or nitrates, organic acid and/or salt of the edible organic acid, and if desired, sweeteners such as corn syrup solids, dextrose, sucrose, among others. Liquid smoke, erythorbate, or ascorbate may also be added to the solution. The level of each ingredient in the solution will be determined by the desired amount of total solution and ingredient to be added to the product. For example, if it is desired that the product contain 10% added solution and 0.5% phosphate and 1% sodium lactate, then the solution must contain 5% phosphate and 10% sodium lactate.

Injection of the polyphosphate solution into a food product can be accomplished by any number of commercially available injection devices well known to those skilled in the art of food processing. A typical device includes a pressurized reservoir that holds the solution connected by a suitable conduit means to a valve-controlled injector head bearing one or more hollow injector needles.

Surface treatments include dip, spray, shower, coating or any treatment that results in the presence of the phosphate or the combination of phosphate and acid salt on the surface of the meat, poultry, or seafood product. The concentration of the phosphate and acid salt will be determined by the levels desired on the surface of the finished product such that antimicrobial efficacy is obtained. In order to improve antimicrobial efficacy, it is desirable to maintain the phosphate and acid salt in intimate contact with the surface of the food. The food may be in the raw state or pre-cooked. This may be accomplished by increasing the viscosity of the solution containing the phosphate and acid salt such that it coats and adheres on the surface of the food. Alternatively, the organic acid and/or salt thereof and phosphate may be part of a gel coating to be applied to the surface of the food. Ingredients, specifically hydrocolloids, starches and proteins that may be used to increase the viscosity of the solution or to form a gel matrix include, but are not restricted to, carrageenan, xanthan gum, locust bean gum, pectin, modified and native starches from various plant sources, gelatin, soy proteins, and dairy-based proteins such as casein arid whey.

Cleaning Compositions

Antimicrobial polyphosphates can be used in cleaning compositions for food, food processing equipment, and food contact surfaces. These compositions can be used to wash the surface of, for example, fruits, vegetables, animal carcasses, food cutting equipment, food preparation tables, packaging material, among others. Washing the surface of fruits and vegetables products with cleaning compositions comprising dilute preparations of antimicrobial polyphosphates helps to avoid wilting and helps to preserve their color and vitamin content. Similarly, changes to the color, flavor, and texture of the surface of animal carcasses are minimized. Surface treatments may be carried out on both cooked and raw products. Raw products may be sold as is or further used as a raw material for cooked products. Cooked products with surface treatment can be packaged for distribution.

The cleaning compositions comprise a mixture of sodium and/or potassium polyphosphates and, optionally, sodium and/or potassium orthophosphates, one or more surfactants, such as a linear alkylbenzene sulfonate (LAS), a salt of fatty acid, an alcohol ethoxylate, etc. Surfactants are disclosed in *Industrial Applications of Surfactants*, D. R. Karsa, ed., The Royal Society of Chemistry, London, 1987, and similar textbooks. The cleaning compositions have a pH of from 4 to 11, and are effective against broad classes of microorganisms including gram-positive and gram-negative bacteria, especially those responsible for foodborne diseases and spoilage of meat and fresh produce.

The polyphosphates have a chain length of 2 to 100. Preferably, the composition contains a mixture of mono-, di- and/or tri-sodium and/or potassium orthophosphate, a linear long chain sodium and/or potassium polyphosphate (chain length 6–50), and a surfactant or a combination of surfactants that are stable over a pH range of 4–11. The compositions may also comprise ethylene diamine tetraacetic acid (EDTA), and/or its salts, and other chelating agents, such as citric acid lactic acid, ascorbic acid and other polycarboxylic acids, and/or their sodium, potassium, and/or calcium salts. The compositions may also comprise low concentrations about 50 to about 200 ppm of peroxy compounds, such as peracetic acid and hydrogen peroxide.

The compositions may be prepared either as a solution, a concentrate, or in dry form to be reconstituted with water at the point of use. Food grade materials should be used to prepare the cleaning compositions. The cleaning composition may be used as a topical spray or as a dip treatment.

The cleaning compositions maintain their antimicrobial efficacy at a pH from 4 to 11. Commercially available products typically require a pH of 10.5 to 12. Lower pH reduces the apparent sliminess of the composition when the composition is rubbed between the fingers. In addition, because of the lower pH, the composition is less likely to cause damage to skin, eyes, and respiratory passages upon contact or inhalation. The compositions are effective even when prepared with hard water.

HIGH POTASSIUM POLYPHOSPHATES

Polyphosphates in which the sodium to potassium ratio is 0.5 to 3.8 may be used in addition to, or in place of sodium polyphosphates, especially in applications in which it is desirable to reduce the sodium content of the food, such as in food for individuals who must control their sodium intake.

Preparation of solutions of sodium and potassium polyphosphates by ion exchange is described in Iler, U.S. Pat. No. 2,557,109, incorporated herein by reference. Glassy polyphosphate of the following composition:

$$(K, Na)_{(n+2)}O(PO_3)_n$$

in which the ratio of potassium to sodium is about 0.5 to 3.8, preferably 1.0 to 3.8, more preferably 2.4 to 3.6; the average value of n is greater than 9; and at least 85% of the phosphate species comprise more than three phosphate units, can be prepared by the following reaction:

A mixture of monopotassium phosphate, monosodium phosphate, and potassium and/or sodium hydroxide is prepared. The potassium/sodium ratio of the mixture should be the same ratio that is desired in the glassy polyphosphate product. Preferably, no ions other than sodium, potassium, the ions derived from phosphate (i.e., $H_2PO_4^-$, $HPO_4^{-2}$, $PO_4^{-3}$), and optionally, hydroxide, are present. If desired, water may also be added to the mixture.

The (K,Na)/P ratio should be between 1.0 and 1.6 and is adjusted for the desired value of n. The smaller the value of this ratio, i.e., the closer this value is to 1.00, the higher the average value of n.

The mixture is placed in a vessel that can withstand the heating conditions, such as a ceramic or alumina vessel, and heated in an appropriate apparatus, such as a muffle furnace. On an industrial scale, the process may be carried out in a bigger furnace, e.g., 8 feet (about 2.4 M) wide by 15 feet (about 4.6 M) long, lined with zircon ramming mix on the bottom designed to withstand a melt temperature of at least 800° C.

The mixture is heated at about 750° C. to drive off water and to form a clear melt. Heating below 600° C. produces materials with insufficient long-chain (n>3) phosphate species. Heating at 780° C. produces material that contains excessive insolubles or difficultly-soluble material that is unacceptable for these applications. Heating should be carried out for about 0.75 to about 1.5 hr. Heating to the required temperature can be carried out in one step or in several stages. After heating, the reaction mixture containing the polyphosphate is, preferably, rapidly cooled so that no crystal growth occurs.

The product is a mixed sodium-potassium polyphosphate glass of formula $(K,Na)_{(n+2)}O(PO_3)_n$, in which n and the ratio of potassium to sodium are as discussed above. The polyphosphate glass contains less than 10% by weight water-insoluble material.

INDUSTRIAL APPLICABILITY

Antimicrobial polyphosphates have numerous application in food processing. They may be used in cleaning compositions, either to wash fruits, vegetables, and animal carcasses or to clean and sanitize food processing equipment. Antimicrobial polyphosphates may be added directly to food products so that they become part of the finished product to be consumed without the need for further rinsing.

Recently the United States Department of Agriculture has issued new regulations concerning new performance standards for food safety of cooked meat and poultry products (9 CFR 381.150). Because of the efficacy of phosphates and polyphosphates against Salmonella and Clostridia, phosphates and polyphosphates may be effectively used in the product to meet the new regulation. By using phosphates, the potential for growth or survival of Salmonella, *Clostridium botulinum,* and *Clostridium perfringens* will be greatly reduced while moisture retention, flavor protection, and emulsion stability provided by phosphates to meat and poultry products will be maintained.

The advantageous properties of this invention can be observed by reference to the following examples which illustrate, but do not limit, the invention.

EXAMPLES

| Glossary | |
|---|---|
| PAA | Peracetic acid |
| Polyphosphate 1 | Glassy, water soluble sodium polyphosphate composed of linear metaphosphate chains (average chain length of 28–34). |
| Polyphosphate 2 | Glassy, water soluble sodium polyphosphate composed of linear metaphosphate chains (average chain length of 21). |
| TSP | Trisodium phosphate |

Examples 1–5

Experimental Procedure

Bacteria were grown individually in trypticase soy broth at 35° C. For each bacterium tested, a 24 hr culture was centrifuged, washed twice with 0.1% peptone water, and resuspended in 10 mL of 0.1% peptone water prior to testing.

All treatments, including controls, contained 0.03% by weight linear alkylbenzene sulfonate. pH was adjusted by addition of either sodium hydroxide or hydrochloric acid, as required. No pH adjustment was made for treatment 9. Treatments were as follows:

| | |
|---|---|
| Treatment 1. | Control. pH = 11.8. |
| Treatment 2. | 0.57% TSP. pH = 11.8. |
| Treatment 3. | 0.57% Polyphosphate 1. pH = 11.8. |
| Treatment 4. | 0.57% Polyphosphate 2. pH = 11.8. |
| Treatment 5. | 0.57% Polyphosphate 1. pH = 6. |
| Treatment 6. | 0.57% Polyphosphate 2. pH = 6. |
| Treatment 7. | 0.57% Polyphosphate 1 + 50 ppm PAA. pH = 11.8. |
| Treatment 8. | 0.57% Polyphosphate 1 + 50 ppm PAA. pH = 6. |
| Treatment 9. | 50 ppm PAA. pH = 2.8. |
| Treatment 10. | 0.57% TSP + 50 ppm PAA. pH = 11.8. |

All phosphate containing treatments were stored at 7° C. prior to testing. For treatments 1–6, a 100 mL aliquot of treatment solution was removed from refrigeration, placed in a sterile Erlenmeyer flask, and allowed to equilibrate to room temperature. For treatments 7–10, a 150 mL aliquot of treatment solution was removed from refrigeration, transferred to an amber passivated bottle, and allowed to equilibrate to room temperature. The tops of these bottles were covered with aluminum foil. Two minutes before testing, 0.14 mL of a 5.5% PAA stock solution was added to each bottle.

To each treatment solution was added 0.1 mL of the appropriate bacteria culture. At intervals of 0.5 min, 1.0 min, and 5.0 min after addition, 1 mL of the inoculated solution was removed and placed in a 9 mL dilution blank. For treatments 1–6 a Butterfield's phosphate dilution blank was used. For treatments 7–10 a Butterfield's phosphate dilution blank containing 1 mL of 0.2 M sodium thiosulfate was used. Samples were diluted and plated with plate count agar (PCA) for 48 hr incubation at 35° C. All inoculum solutions were also plated onto PCA to determine initial inoculum levels. After incubation, the colonies on plates were enumerated.

Five species of bacteria were tested: *Escherichia coli* 0157:H7, a gram-negative bacterium; *Staphylococcus aureus*, a gram-positive bacterium; *Listeria monocytogenes*, a gram-positive bacterium; *Salmonella typhimurium*, a gram-negative bacterium; and *Pseudomonas aeruginosa*, a gram-negative bacterium.

The treatments were also tested against a mixture of yeasts and molds, but none of the treatments were effective against either yeasts or molds within the five-minute exposure in the treatment solution.

Treatment of *Escherichia coli*

Figure 1:
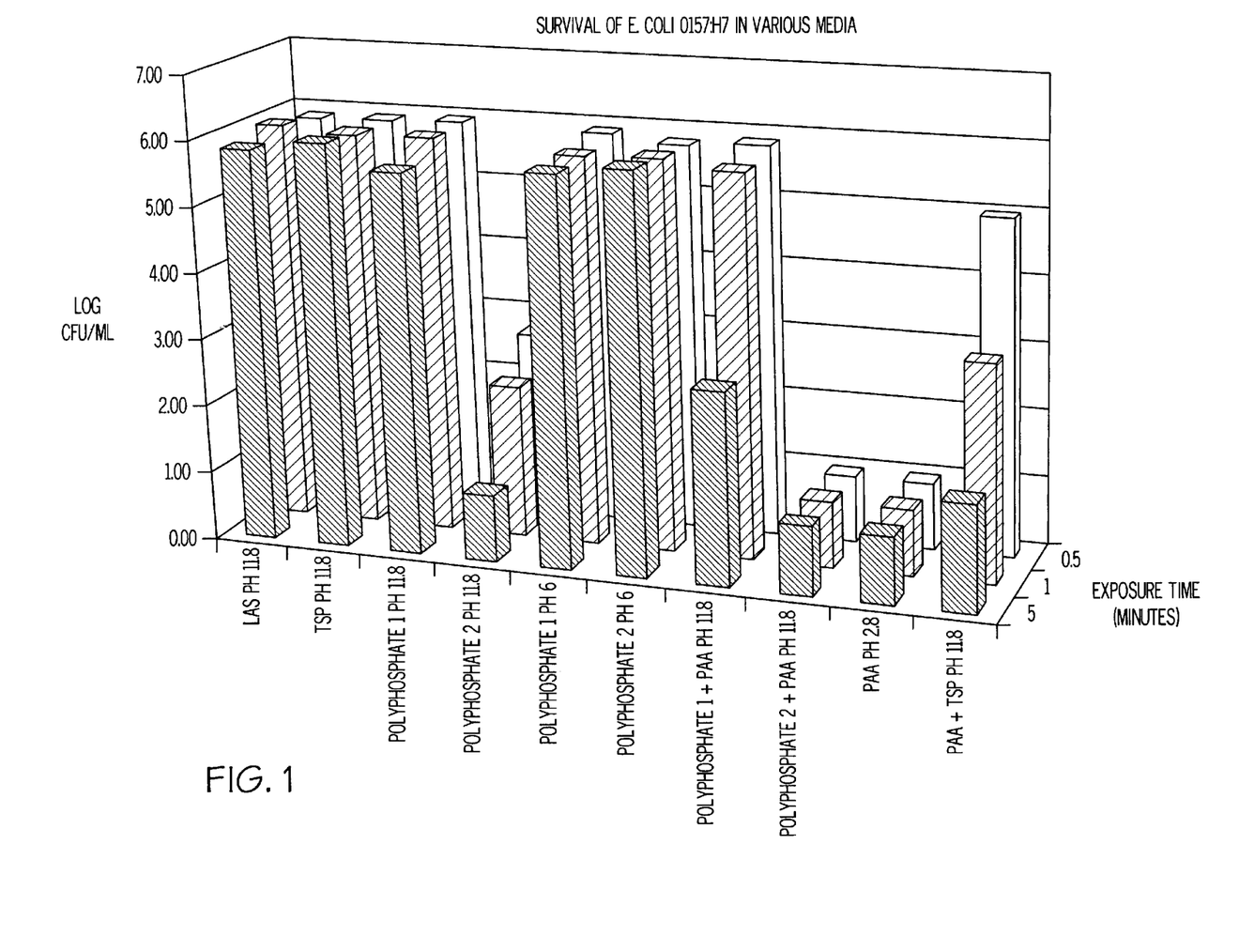
FIG. 1 shows the effect of phosphates on the survival of Escherichia coli 0157:H7.

*Escherichia coli* 0157:H7 is more tolerant to acidic environments than other foodborne pathogens, and, therefore, poses a greater hazard. It has been known to survive in fermented sausage, mayonnaise, and apple cider. It has been reported that 1.5% organic acid sprays are not effective against this organism on beef. The infective dose appears to be very low, i.e., less than 1 cell/g of food. Treatment of *E. coli* is shown in Table 1 and FIG. 1.

TABLE 1

Treatment of *Escherichia coli* 0157:H7

| Treatment | time (min) | log count | log reduction |
|---|---|---|---|
| None | 0 | 6.09 | — |
| 1 | 0.5 | 5.92 | 0.17 |
| | 1 | 6.04 | 0.05 |
| | 5 | 5.89 | 0.20 |
| 2 | 0.5 | 5.96 | 0.13 |
| | 1 | 5.96 | 0.13 |
| | 5 | 6.05 | 0.04 |

TABLE 1-continued

Treatment of *Escherichia coli* 0157:H7

| Treatment | time (min) | log count | log reduction |
|---|---|---|---|
| 3 | 0.5 | 6.00 | 0.10 |
| | 1 | 5.99 | 0.10 |
| | 5 | 5.69 | 0.40 |
| 4 | 0.5 | 2.79 | 3.31 |
| | 1 | 2.32 | 3.77 |
| | 5 | <1 | >5.09 |
| 5 | 0.5 | 5.95 | 0.15 |
| | 1 | 5.85 | 0.24 |
| | 5 | 5.83 | 0.27 |
| 6 | 0.5 | 5.85 | 0.24 |
| | 1 | 5.88 | 0.21 |
| | 5 | 5.98 | 0.12 |
| 7 | 0.5 | 5.90 | 0.19 |
| | 1 | 5.76 | 0.33 |
| | 5 | 2.89 | 3.21 |
| 8 | 0.5 | <1 | >5.09 |
| | 1 | <1 | >5.09 |
| | 5 | <1 | >5.09 |
| 9 | 0.5 | <1 | >5.09 |
| | 1 | <1 | >5.09 |
| | 5 | <1 | >5.09 |
| 10 | 0.5 | 5.05 | 1.04 |
| | 1 | 3.27 | 2.83 |
| | 5 | 1.60 | 4.49 |

Treatment of *Staphylococcus aureus*

Figure 2:
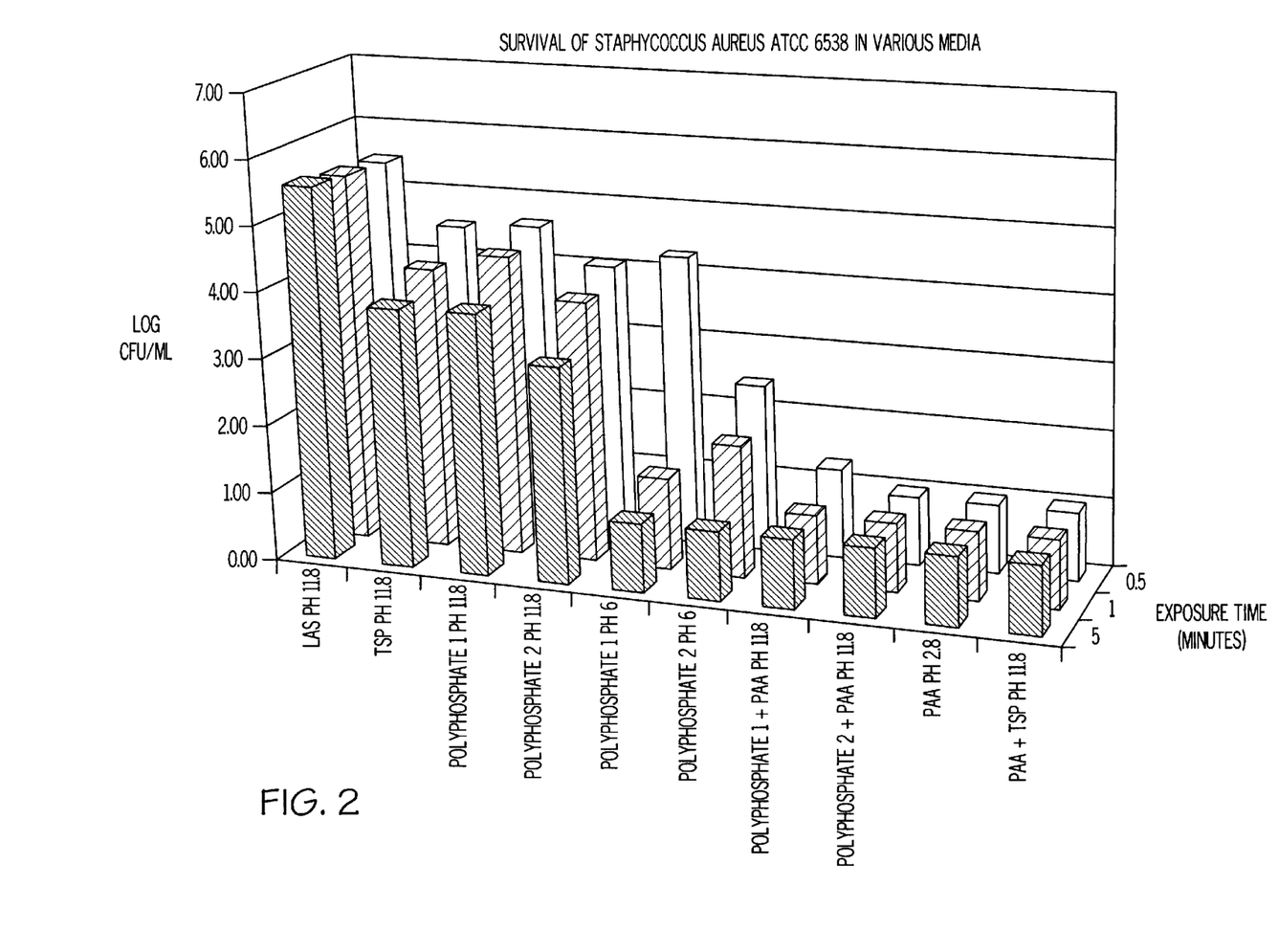
FIG. 2 shows the effect of phosphates on the survival of Staphylococcus aureus ATCC 6538.

*S. aureus* is a foodborne pathogen that causes gastroenteritis as a result of ingesting the enterotoxin. Treatment of *S. aureus* is shown in Table 2 and FIG. 2.

TABLE 2

Treatment of *Staphylococcus aureus* ATCC 6538

| Treatment | time (min) | log count | log reduction |
|---|---|---|---|
| None | 0 | 4.94 | — |
| 1 | 0.5 | 5.46 | 0 |
| | 1 | 5.52 | 0 |
| | 5 | 5.57 | 0 |
| 2 | 0.5 | 4.53 | 0.41 |
| | 1 | 4.14 | 0.80 |
| | 5 | 3.83 | 1.11 |
| 3 | 0.5 | 4.61 | 0.33 |
| | 1 | 4.41 | 0.53 |
| | 5 | 3.88 | 1.07 |
| 4 | 0.5 | 4.10 | 0.85 |
| | 1 | 3.85 | 1.10 |
| | 5 | 3.18 | 1.76 |
| 5 | 0.5 | 4.30 | 0.64 |
| | 1 | 1.30 | 3.64 |
| | 5 | <1 | >3.94 |
| 6 | 0.5 | 2.46 | 2.48 |
| | 1 | 1.90 | 3.04 |
| | 5 | 1.00 | 3.94 |
| 7 | 0.5 | 1.30 | 3.64 |
| | 1 | 1.00 | 3.94 |
| | 5 | <1 | >3.94 |
| 8 | 0.5 | <1 | >3.94 |
| | 1 | <1 | >3.94 |
| | 5 | <1 | >3.94 |
| 9 | 0.5 | <1 | >3.94 |
| | 1 | <1 | >3.94 |
| | 5 | <1 | >3.94 |
| 10 | 0.5 | <1 | >3.94 |
| | 1 | <1 | >3.94 |
| | 5 | <1 | >3.94 |

Treatment of *Salmonella typhimurium*

Figure 3:
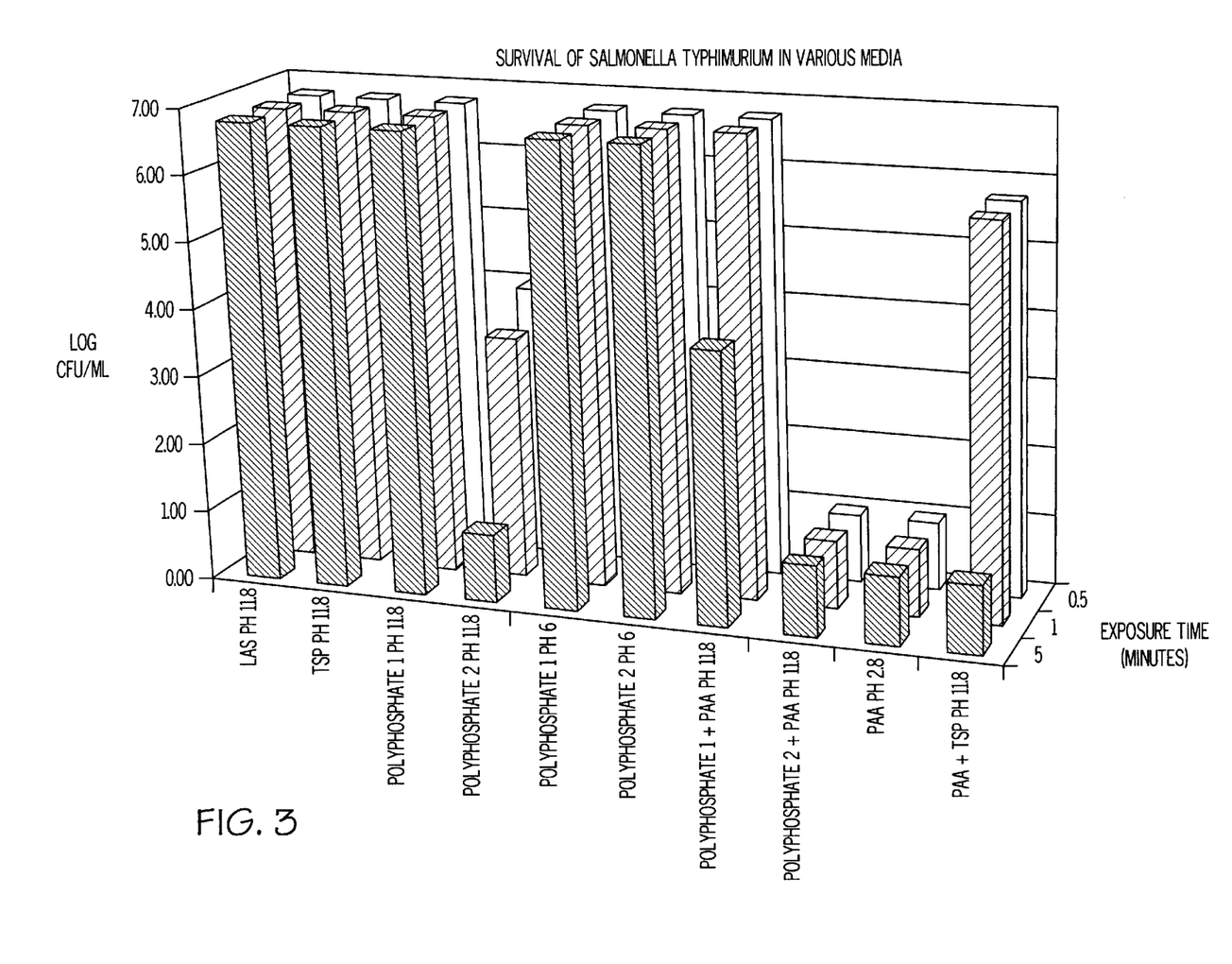
FIG. 3 shows the effect of phosphates on the survival of Salmonella typhimurium ATCC 14020.

*S. typhimurium* is a common source of foodborne disease. Treatment of *S. typhimurium* is shown in Table 3 and FIG. 3.

TABLE 3

**Treatment of *Salmonella typhimurium* ATCC 14020**

| Treatment | time (min) | log count | log reduction |
|---|---|---|---|
| None | 0 | 6.33 | — |
| 1 | 0.5 | >6.79 | 0 |
|  | 1 | >6.79 | 0 |
|  | 5 | >6.79 | 0 |
| 2 | 0.5 | >6.79 | 0 |
|  | 1 | >6.79 | 0 |
|  | 5 | >6.79 | 0 |
| 3 | 0.5 | >6.79 | 0 |
|  | 1 | >6.79 | 0 |
|  | 5 | >6.79 | 0 |
| 4 | 0.5 | 4.05 | 2.28 |
|  | 1 | 3.62 | 2.71 |
|  | 5 | <1.00 | >5.33 |
| 5 | 0.5 | >6.79 | 0 |
|  | 1 | >6.79 | 0 |
|  | 5 | >6.79 | 0 |
| 6 | 0.5 | >6.79 | 0 |
|  | 1 | >6.79 | 0 |
|  | 5 | >6.79 | 0 |
| 7 | 0.5 | >6.79 | 0 |
|  | 1 | >6.79 | 0 |
|  | 5 | 4.03 | 2.30 |
| 8 | 0.5 | 1 | 5.33 |
|  | 1 | <1 | >5.33 |
|  | 5 | <1 | >5.33 |
| 9 | 0.5 | <1 | >5.33 |
|  | 1 | <1 | >5.33 |
|  | 5 | <1 | >5.33 |
| 10 | 0.5 | >5.79 | 0 |
|  | 1 | >5.79 | 0 |
|  | 5 | 1.00 | 5.33 |

Treatment of *Listeria monocytogenes*

Figure 4:
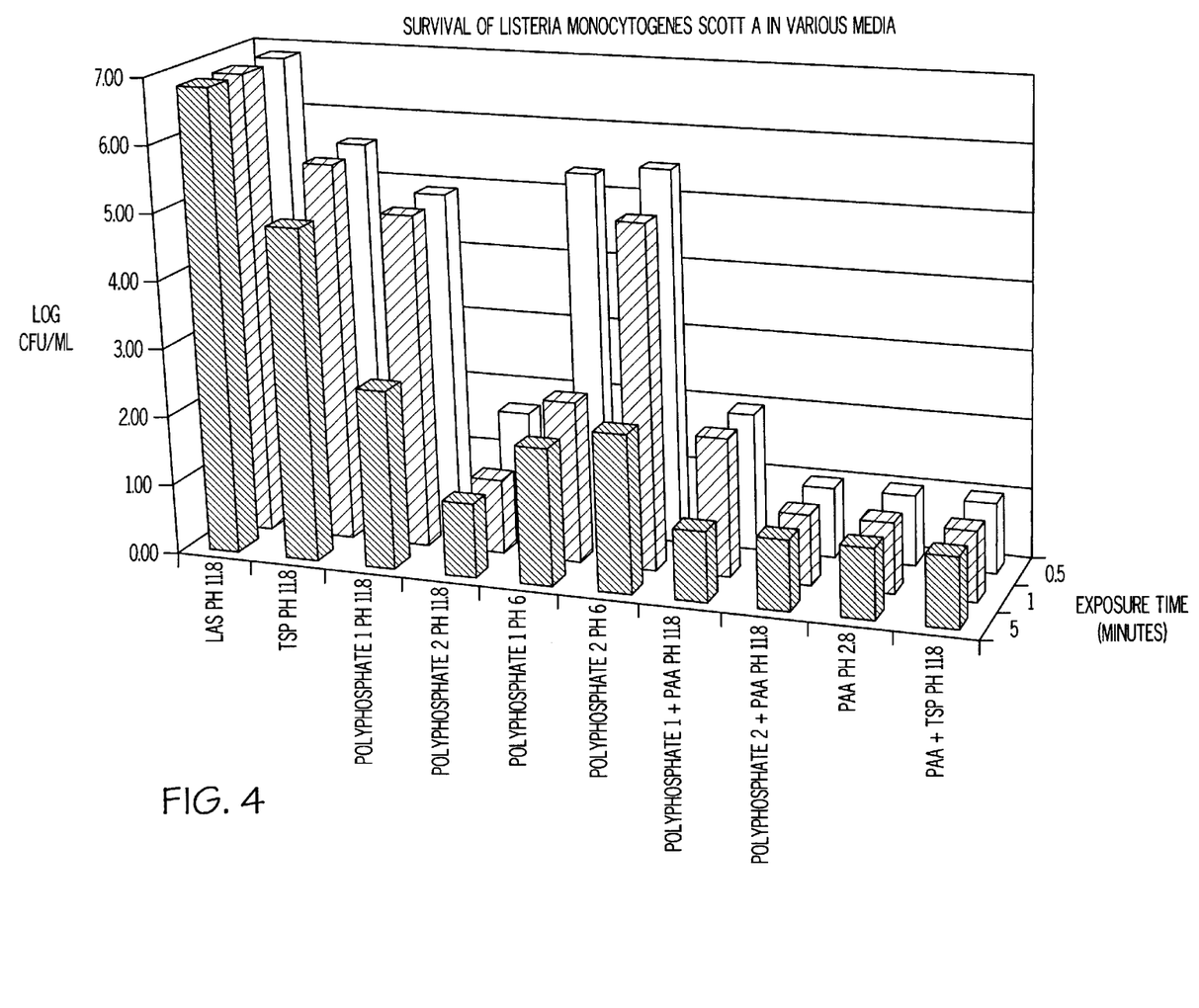
FIG. 4 shows the effect of phosphates on the survival of Listeria monocytogenes Scott A.

In the last decade, listeriosis, caused by *L. monocytogenes,* has emerged a major foodborne disease. Because the bacterium is resistant to low pH and high sodium chloride concentrations and grows at refrigeration temperatures, it is very difficult to eradicate from food processing plants. Treatment of *L. monocytogenes* is shown in Table 4 and FIG. 4.

TABLE 4

**Treatment of *Listeria monocytogenes* Scott A**

| Treatment | time (min) | log count | log reduction |
|---|---|---|---|
| None | 0 | 5.85 | — |
| 1 | 0.5 | >6.79 | 0 |
|  | 1 | >6.79 | 0 |
|  | 5 | >6.79 | 0 |
| 2 | 0.5 | 5.59 | 0.26 |
|  | 1 | 5.54 | 0.31 |
|  | 5 | 4.86 | 0.99 |
| 3 | 0.5 | 4.90 | 0.95 |
|  | 1 | 4.86 | 0.99 |
|  | 5 | 2.60 | 3.25 |
| 4 | 0.5 | 1.70 | 4.15 |
|  | 1 | 1.00 | 4.85 |
|  | 5 | <1 | >4.85 |
| 5 | 0.5 | 5.40 | 0.45 |
|  | 1 | 2.30 | 3.55 |
|  | 5 | 2.00 | 3.85 |
| 6 | 0.5 | 5.54 | 0.31 |
|  | 1 | 5.00 | 0.85 |
|  | 5 | 2.30 | 3.55 |
| 7 | 0.5 | <2 | >3.85 |
|  | 1 | <1 | >4.85 |
|  | 5 | <1 | >4.85 |
| 8 | 0.5 | <1 | >4.85 |
|  | 1 | <1 | >4.85 |
|  | 5 | <1 | >4.85 |
| 9 | 0.5 | <1 | >4.85 |
|  | 1 | <1 | >4.85 |
|  | 5 | <1 | >4.85 |
| 10 | 0.5 | <1 | 3.85 |
|  | 1 | <1 | 4.85 |
|  | 5 | <1 | >4.85 |

Treatment of *Pseudomonas aeruginosa*

Figure 5:
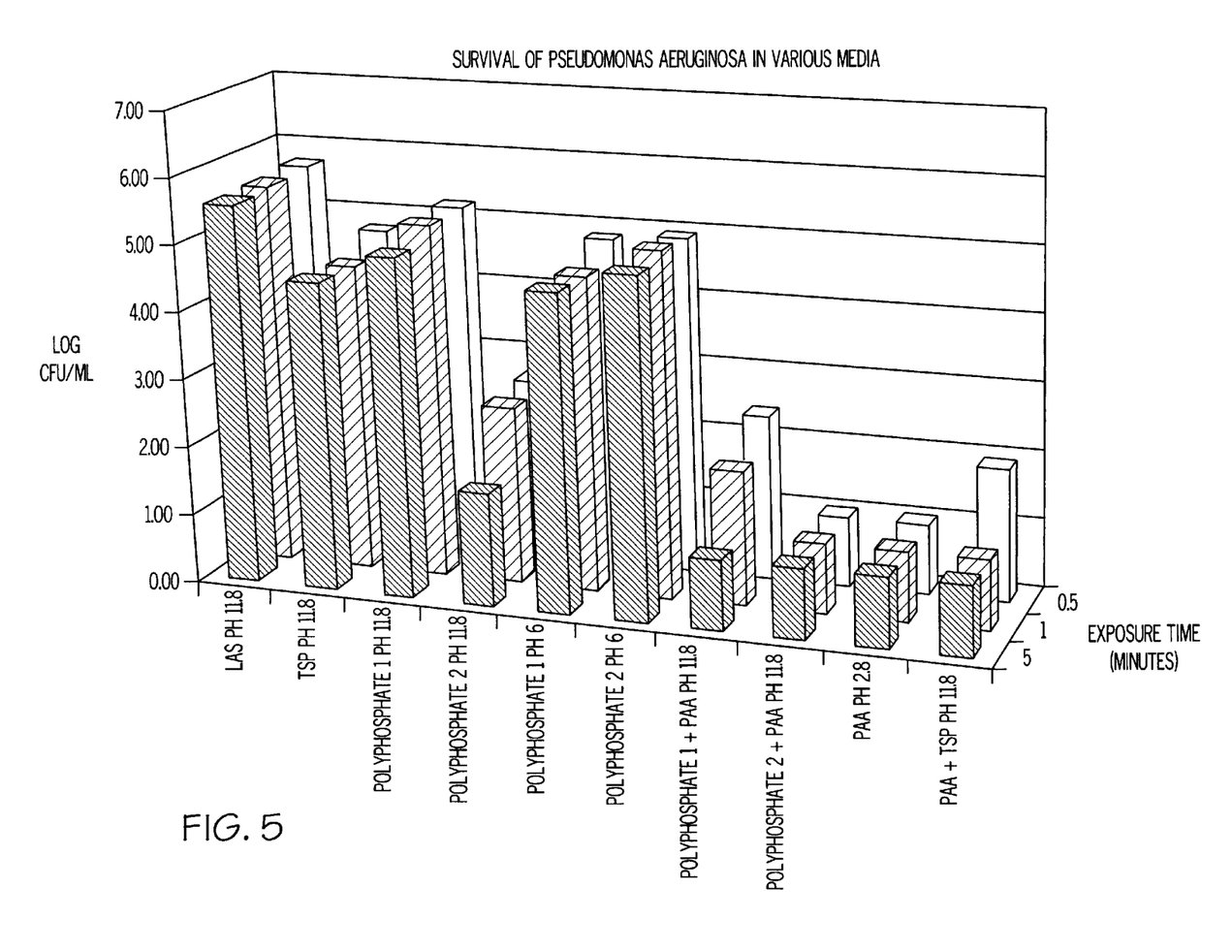
FIG. 5 shows the effect of phosphates on the survival of Pseudomonas aeruginosa.

Pseudomonas are common spoilage bacteria or fresh meat an poultry products, especially those exposed to temperature abuse. Treatment of *P. aeruginosa,* a species resistant to phenolic antioxidants, is shown in Table 5 and FIG. 5.

TABLE 5

**Treatment of *Pseudomonas aeruginosa***

| Treatment | time (min) | log count | log reduction |
|---|---|---|---|
| None | 0 | 5.82 | — |
| 1 | 0.5 | 5.76 | 0 |
|  | 1 | 5.70 | 0 |
|  | 5 | 5.66 | 0 |
| 2 | 0.5 | 4.86 | 0.96 |
|  | 1 | 4.58 | 1.24 |
|  | 5 | 4.59 | 1.23 |
| 3 | 0.5 | 5.25 | 0.57 |
|  | 1 | 5.27 | 0.55 |
|  | 5 | 5.05 | 0.77 |
| 4 | 0.5 | 2.70 | 3.12 |
|  | 1 | 2.60 | 3.22 |
|  | 5 | 1.70 | 4.12 |
| 5 | 0.5 | 4.94 | 0.88 |
|  | 1 | 4.67 | 1.15 |
|  | 5 | 4.72 | 1.10 |
| 6 | 0.5 | 4.99 | 0.83 |
|  | 1 | 5.10 | 0.72 |
|  | 5 | 5.03 | 0.79 |
| 7 | 0.5 | 2.49 | 3.33 |
|  | 1 | 2.00 | 3.82 |
|  | 5 | <1 | >4.82 |
| 8 | 0.5 | <1 | >4.82 |
|  | 1 | <1 | >4.82 |
|  | 5 | <1 | >4.82 |
| 9 | 0.5 | <1 | >4.82 |
|  | 1 | <1 | >4.82 |
|  | 5 | <1 | >4.82 |
| 10 | 0.5 | 2.00 | 3.82 |
|  | 1 | 1.00 | 4.82 |
|  | 5 | <1 | >4.82 |

SUMMARY OF RESULTS

Treatment 1. Control. pH=11.8. Not effective against any of the bacteria tested.

Treatment 2. 0.57% TSP. pH=11.8. Not effective against any of the bacteria tested.

Treatment 3. 0.57% Polyphosphate 1. pH=11.8. Somewhat effective against *Listeria monocytogenes,* with a 3.24 log reduction at 5 min. Not effective against any of the other bacteria tested.

Treatment 4. 0.57% Polyphosphate 2. pH=11.8. Effective against *Listeria monocytogenes,* with a 4.8 log reduction at 1 min. Also effective against *Escherichia coli* 0157:H7 and *Salmonella typhimurium,* with >5 log reductions at 5 min. Somewhat effective against *Pseudomonas aeruginosa,* with a 4.1 log reduction at 5 min.

Treatment 5. 0.57% Polyphosphate 1. pH=6. Effective against *Staphylococcus aureus*, with a >3.9 log reduction at 5 min. Not effective against any of the other bacteria tested.

Treatment 6. 0.57% Polyphosphate 2. pH=6. Effective against *Staphylococcus aureus* and *Listeria monocytogenes* with 4.0 and 3.5 log reductions at 5 min, respectively. Not effective against any of the other bacteria tested.

Treatment 7. 0.57% Polyphosphate 1+50 ppm PAA. pH=11.8. Effective against *Listeria monocytogenes*, with a >3.8 log reduction at 0.5 min and >3.8 log reduction at 5 min. Effective against *Staphylococcus aureus* and *Pseudomonas aeruginosa*, with >3.8 and >4.8 log reductions at 5 min, respectively. Somewhat effective against *Escherichia coli* 0157:H7 and *Salmonella typhimurium*, with log reductions at 5 min of 3.2 and 2.3, respectively.

Treatment 8. 0.57% Polyphosphate 1+50 ppm PAA. pH=6. Very effective against *Escherichia coli* 0157:H7, *Staphylococcus aureus*, *Listeria monocytogenes*, and *Pseudomonas aeruginosa*, with no cells recovered at 0.5 min. Also very effective against *Salmonella typhimurium*, with a 5.3 log reduction at 0.5 min and >5.33 at 1 min.

Treatment 9. 50 ppm PAA. pH=2.8. Very effective against *Escherichia coli* 0157:H7, *Salmonella typhimurium*, *Listeria monocytogenes*, and *Pseudomonas aeruginosa*, with no cells recovered at 0.5 min.

Treatment 10. 0.57% TSP+50 ppm PAA. pH=11.8. Effective against *Staphylococcus aureus* and *Listeria monocytogenes*, with no cells recovered at 0.5 min. Effective against *Escherichia coli* 0157:H7 and *Salmonella typhimurium*, with log reductions at 5 min of 4.5 and 5.33, respectively.

Example 6

This Example shows the effect of phosphates on the growth of microorganisms in cooked meat.

Sample Preparation

Seven batches 40-pound (about 18.2 Kg) of cooked sectioned and formed boneless ham were manufactured to meet the following specifications: moisture, 71.2–73.7%; protein, 18.1–19.8%; fat, 3.66–6.31%; salt, 2.0%; and phosphate, 0.4%. The hams were manufactured to conform to the standards of identity for a cooked ham with a minimum of 18.5% protein fat free (PFF). The phosphate salts (0.4% by weight) indicated in Table 6 were added to six of the hams. The hams were injection pumped to 10% by weight with a standard brine solution containing 4% phosphate, 17.7% salt (NaCl), 5.0% sucrose, 2.5% prague powder (6.25% sodium nitrite), and 0.55% sodium erythorbate. After injection, the hams were vacuum-tumbled for 45 min, stuffed into 6.5-in (about 16.5 cm) diameter fibrous casings, and then cooked to an internal temperature of 71.1° C. Cooked hams were chilled for 8 hr at 0° C., vacuum packaged, and stored at 0° C. for 8 weeks.

Microbiological Analysis

Sample homogenate was prepared by blending 11 g of ham with 99 mL of sterile 0.1% peptone diluent and agitating for 1 min in a stomacher. Serial dilutions were prepared by transferring 1.0 mL aliquots of the sample diluent to 9 mL of sterile 0.1% peptone. The appropriate dilutions were plated on plate count agar. The plates were incubated at 7° C. for 10 days.

Results for psychrotrophic organisms are shown in Table 6. All phosphate treatments contained significantly fewer psychrotrophic organisms compared to the control without added phosphate. The results for the various phosphate treatments are not considered to be significantly different.

TABLE 6

Growth of Psychrotrophic Microorganisms in Sectioned and Formed Ham after 8 Weeks Storage at 0° C.

| Phosphate Added | log (colony forming units)/g |
|---|---|
| None | 3.97 |
| Sodium tripolyphosphate (pH about 9.8) | 1.58 |
| Sodium tripolyphosphate (pH about 9.8) | 1.84 |
| Sodium polyphosphate blend (pH about 10) | 1.83 |
| Sodium polyphosphate blend (pH about 9.5) | 1.91 |
| Sodium polyphosphate blend (pH about 7) | 2.15 |
| Sodium polyphosphate blend (pH about 7) | 2.82 |

Sensory Evaluation

One ¾" (about 1.8 cm) slice was removed and placed on white absorbent paper for color acceptability evaluation. Two ½" (about 1.2 cm) slices were removed for sensory evaluation. The slices were placed in a template and 1.0 cm×2.0 cm samples were prepared. Each panelist received 1 sample/treatment. The control and three treatments were served at each session. Crackers and apple juice were served. Prior to testing, two sessions of training were conducted that included discussions on juiciness, ham flavor intensity, off-flavor, and color acceptability.

The sensory characteristics and objective color properties of the hams were not adversely affected by the phosphate treatments. In addition, added phosphate increased cooking and processing yields.

Example 7

This Example shows the effect of phosphates on the growth of microorganisms in cooked meat.

Sample Preparation

Five 16 Kg batches of restructured ham were prepared. Fresh whole pork hams were skinned, boned, sectioned into muscles, and each muscle trimmed to remove all trimmable connective tissue and subcutaneous and intramuscular fat. The muscles were injection pumped 10% by weigh with a standard brine solution containing the desired amount of phosphate, 17.7% salt (NaCl), 5.0% sucrose, 2.5% prague powder (6.25% sodium nitrite), and 0.55% sodium erythorbate. Phosphate was added to four or the five samples to obtain the desired level in the cooked product. The pumped muscles were macerated manually to facilitate brine absorption; tumbled; and stuffed into fibrous casings in 908.0 g chubs. The hams were weighed and then cooked to 71.1° C. internal temperature. Cooked hams were chilled for 24 hr at 0° C., vacuum packaged, and stored at 1.11° C. for 8 weeks.

Microbiological Analysis

Sample homogenate was prepared by blending 11 g of ham with 99 mL of sterile 0.1% peptone diluent and agitating for 1 min in a stomacher. Serial dilutions were prepared by transferring 1.0 mL aliquots of the sample diluent to 9 mL of sterile 0.1% peptone. The appropriate dilutions were plated onto 3M Petrifilm plates for aerobic plate count and psychrotrophic organisms, or APT agar for lactic acid organisms. The plates were incubated at either 35° C. for 48 hr, 20° C. for 5 days, or 30° C. for 48 hr for aerobic plate count, psychrotrophic organisms, and lactic acid organisms, respectively. Duplicate samples were analyzed for each treatment. Results are shown in Tables 7, 8, and 9.

TABLE 7

Growth of Psychrotrophic Microorganisms in
Sectioned and Formed Ham After 8 Weeks Storage at 1.11° C.

| Phosphate Added | log (colony forming units)/g |
| --- | --- |
| None | 7.79 |
| 0.4% Sodium tripolyphosphate | 7.8 |
| 1.0% Sodium tripolyphosphate | 5.91 |
| 1.0% Sodium acid pyrophosphate | 5.28 |
| 1.0% Sodium hexametaphosphate | 4.62 |

TABLE 8

Aerobic Plate Count in Sectioned and Formed Ham
After 8 Weeks Storage at 1.11° C.

| Phosphate Added | log (colony forming units)/g |
| --- | --- |
| None | 6.03 |
| 0.4% Sodium tripolyphosphate | 6.69 |
| 1.0% Sodium tripolyphosphate | 5.67 |
| 1.0% Sodium acid pyrophosphate | 4.49 |
| 1.0% Sodium hexametaphosphate | 4.55 |

TABLE 9

Growth of Lactic Acid Organisms in Sectioned and Formed Ham
After 8 Weeks Storage at 1.11° C.

| Phosphate Added | log (colony forming units)/g |
| --- | --- |
| None | 7.42 |
| 0.4% Sodium tripolyphosphate | 6.62 |
| 1.0% Sodium tripolyphosphate | 6.70 |
| 1.0% Sodium acid pyrophosphate | 5.38 |
| 1.0% Sodium hexametaphosphate | 6.24 |

Having described the invention, we now claim the following and their equivalents.

What is claimed is:

1. A method for preventing the growth of *Listeria monocytogenes, Pseudonomas aeruginosa* and *Escherichia coli* in meat, poultry, and seafood products, the method comprising:
    adding to the meat, poultry, or seafood products an aqueous solution with a pH of 7–11 consisting of a polyphosphate and optionally an organic acid and/or salt of the organic acid;
    wherein:
        after addition of the aqueous solution the meat, seafood, or poultry products comprise 0.01% to 2% by weight polyphosphate;
        the polyphosphate is a sodium polyphosphate, a potassium polyphosphate, a mixed sodium/potassium polyphosphate, or a mixture thereof; and
        the polyphosphate is water soluble and has a chain length of at least two.

2. The method of claim 1 in which, after addition of the aqueous solution, the meat, seafood, or poultry product comprises 0.3% to 2.0% by weight organic acid and/or salt of the organic acid and 0.05% to 1.0% polyphosphate.

3. A method for washing food, the method comprising:
    exposing the surface of the food, to an antimicrobial cleaning composition;
    in which the antimicrobial cleaning composition consists of a mixture of:
        alkali metal orthophosphate salt, in which the alkali metal is sodium, potassium, or a mixture thereof;
        a linear long chain alkali metal polyphosphate of chain length 2–100, in which the alkali metal is sodium, potassium, or a mixture thereof; and
        a surfactant or a combination of surfactants that are stable over a pH range of 4–11.

4. The method of claim 3 in which the cleaning composition additionally comprises a chelating agent.

5. The method of claim 4 in which the chelating agent is a polycarboxylic acid.

6. The method of claim 5 in which the polycarboxylic acid is selected from the group consisting of ethylene diamine tetraacetic acid, citric acid, lactic acid, ascorbic acid, and sodium, potassium, and calcium salts thereof.

7. The method of claim 1 wherein said aqueous solution further consists of an edible organic acid and/or a salt of an edible organic acid and wherein after addition of said aqueous solution the meat, seafood or poultry product further comprises 0.3% to 7% by weight acid salt.

8. The method of claim 7 wherein said organic acid comprises lactic acid.

9. A food composition selected from the group consisting of meat, poultry and seafood products, wherein said food composition comprises 0.01% to 2% by weight polyphosphate;
    said food composition is obtained by adding to the meat, poultry, or seafood products an aqueous solution of pH 7–11 consisting of a polyphosphate;
    said polyphosphate is a sodium polyphosphate, a potassium polyphosphate, a mixed sodium/potassium polyphosphate, or a mixture thereof; and
    said polyphosphate is water soluble and has a chain length of at least two.

10. The food composition of claim 9 wherein said food composition further comprises 0.3% to 7% by weight edible organic acid salt; and said composition is obtained by adding to the meat, poultry or seafood product said aqueous solution further consisting of an organic acid and/or a salt of an organic acid.

11. The food composition of claim 10 wherein said food composition comprises 0.3% to 2.0% by weight organic acid and/or salt of said organic acid and 0.05% to 1.0% polyphosphate.

12. The food composition of claim 10 wherein said organic acid comprises lactic acid.

13. The food composition of claim 9 wherein said polyphosphate comprises hexametaphosphate.

14. A method for preventing the growth of *Listeria monocytogenes, Pseudonomas aeruginosa* and *Escherichia coli* in meat, poultry, and seafood products, the method comprising:
    adding to the meat, poultry, or seafood products a composition with a pH of 7–11 consisting of hexamethaphosphate and optionally an organic acid and/or salt of the organic acid in aqueous solution;
    wherein: C
        after addition of the aqueous solution the meat, seafood, or poultry products comprise 0.01% to 2% by weight hexametaphosphate;
        the hexametaphosphate is a sodium hexametaphosphate, a potassium hexametaphosphate, a mixed sodium/potassium hexametaphosphate, or a mixture thereof; and
        the hexametaphosphate is water soluble.

15. The method of claim 14 wherein, after addition of the aqueous solution, the meat, seafood, or poultry product comprises 0.3% to 2.0% by weight organic acid and/or salt of the organic acid and 0.05% to 1.0% polyphosphate.

16. The method of claim 15 wherein said organic acid comprises lactic acid.

\* \* \* \* \*